United States Patent [19]

Masamizu et al.

[11] Patent Number: 4,742,086
[45] Date of Patent: May 3, 1988

[54] PROCESS FOR MANUFACTURING POROUS POLYMER

[75] Inventors: Koji Masamizu, Houya; Shinya Hirokawa, Chiba; Sanae Fujita, Tokyo, all of Japan

[73] Assignee: Lion Corporation, Tokyo, Japan

[21] Appl. No.: 922,991

[22] Filed: Oct. 24, 1986

[30] Foreign Application Priority Data

Nov. 2, 1985 [JP] Japan .............................. 60-246623
Jul. 17, 1986 [JP] Japan .............................. 61-168806
Sep. 1, 1986 [JP] Japan .............................. 61-205281

[51] Int. Cl.$^4$ .............................. C08J 9/26; C08J 9/28
[52] U.S. Cl. .............................. 521/62; 521/63; 521/64; 521/61; 524/37; 524/42; 524/543; 524/555; 524/556; 524/557; 524/801; 524/803
[58] Field of Search .............................. 521/62, 63, 64, 61

[56] References Cited

U.S. PATENT DOCUMENTS 4,328,149  5/1982  Morse et al.
4,489,174 12/1984  Karickhoff .............................. 521/64

Primary Examiner—Morton Foelak
Attorney, Agent, or Firm—Burns, Doane, Swecker & Mathis

[57] ABSTRACT

The present invention provides a process for manufacturing a porous polymer containing many voids in its interior, which has a small apparent specific gravity and is superior in terms of water absorbing properties, permeability and elasticity. The process comprises (1) forming O/W emulsion by using a water soluble surfactant wherein an inner phase of the O/W emulsion is a hydrophobic phase and an outer phase thereof is a water phase containing at least one water-soluble polymerizable monomer; (2) adding said O/W emulsion to a hydrophobic dispersing medium containing an oil-soluble surfactant to form O/W/O emulsion; and (3) polymerizing the monomer.

14 Claims, 2 Drawing Sheets

PROCESS FOR MANUFACTURING POROUS POLYMER

BACKGROUND OF THE INVENTION (1) Field of the Invention

The present invention relates to a process for manufacturing a porous polymer having many voids in its interior, in particular a porous polymer having small apparent specific gravity and being superior in terms of water-absorbing properties, permeability and elasticity. The present invention also relates to an absorbing article such as a sanitary napkin or a paper daper, which comprises an absorbing layer containing the porous polymer.

(2) Prior Art of the Invention

There have been known various methods of manufacturing a water-absorbing resin in which an unsaturated ethylene monomer such as acrylic acid or acrylic acid alkali metal salt is polymerized by reversed phase suspension polymerization. For example, employing reversed phase suspension polymerization or reversed phase emulsion polymerization, a polymer dispersant (disclosed in Japanese Patent Public Disclosure (KOKAI) No. 167307/1982) or a surfactant (disclosed in Japanese Patent Public Disclosure No. 32641/1983) is added to an aqueous solution containing vinyl monomer to improve the wettability of a water absorbing polymer. However, when the above-mentioned water-absorbing polymer is used, for example, as a water-absorbing agent for a sanitary napkin or a paper diaper, the water-absorbing polymer is required to have practical properties such as good elasticity, small apparent specific gravity to be easily mixed with cotton-like pulp, good water-absorbing properties and high permeability. The water-absorbing polymers manufactured by the conventional methods do not always have the above practical properties.

On the other hand, Japanese Patent Public Disclosure No. 193901/1984 discloses a process for manufacturing spherical polymer having spherical voids of an average diameter of 0.5 to 50 microns, in particular, a raw material suitable for use in cosmetics, wherein a nonionic surfactant is added to a monomer phase and an ionic surfactant is also added to a water phase in polymerization of hydrophobic monomer in aqueous dispersing medium to form water phase/monomer phase/water phase (so-called W/O/W type emulsion), after which the monomer is polymerized. However, a water-absorbing polymer having the above-mentioned practical properties cannot be manufactured by applying the above method without modification to polymerization of water-soluble monomer.

SUMMARY OF THE INVENTION

The present invention has been accomplished based on the discovery that a water-soluble polymerizable monomer is not polymerized by the conventional reverse phase suspension polymerization or reverse phase emulsion polymerization, but is polymerized after formation of O/W/O type emulsion having a phase containing the monomer as an intermediate phase, so that porous polymer can effectively be manufactured.

It is, therefore, a primary object of the invention to manufacture a polymer having many voids in its interior.

Another object of the present invention is to manufacture a polymer having small apparent specific gravity and being superior in terms of water-absorbing properties, permeability and elasticity.

Another object of the present invention is to manufacture a spherical water-absorbing polymer having the above-mentioned properties.

Another object of the present invention is to provide an absorbing article comprising an absorbing layer containing the porous layer.

These and other objects of the present invention will be clear from the following description.

In accordance with the present invention, there is provided a process for preparing a porous polymer comprising the steps of:

(1) forming O/W emulsion by using a water-soluble sufactant or a water-soluble high-molecular dispersant wherein an inner phase of the O/W emulsion is a hydrophobic phase and an outer phase thereof is a water phase containing at least one water-soluble polymerizable monomer;

(2) adding said O/W emulsion to a hydrophobic dispersing medium containing an oil-soluble surfactant or a oil-soluble high-molecular dispersant to form O/W/O emulsion; and (3) polymerizing the monomer

DESCRIPTION OF THE PREFERRED EMBODIMENTS

Examples of water-soluble polymerizable monomers usable in the present invention include vinyl monomer having a polymerizable unsaturated group such a olefin unsaturated carboxylic acid, olefin unsaturated sulfonic acid, olefin unsaturated amine or olefin unsaturated ether. Among these, examples of vinyl monomers having sulfonic group include unsaturated sulfonic acids such as acryl amido methyl propane sulfonic acid, allyl sulfonic acid, and examples of vinyl monomers having amino group include unsaturated amines such as dimethyl aminoethyl methacrylate. Examples of vinyl monomers having carboxyl group or carboxylate group also include unsaturated carboxylic acid such as acrylic acid, methacrylic acid, maleic acid and fumaric acid; unsaturated carboxylate such as acrylate, methacrylate, malate, fumarate, methoxypolyethyleneglycol methacrylate, phenoxypolyethyleneglycol methacrylate. Furthermore, examples of water-soluble salts of acrylic acid, methacrylic acid or the like include alkaline metal salts, alkaline earth metal salts and ammonium salts of unsaturated carborylic acids. In the present invention, it is preferable to use only the above-mentioned water-soluble monomer as a polymerizable monomer. There can also be used water-insoluble monomers which are co-polymerizable with the water-soluble vinyl monomers, e.g., alkyl (having 1 to 18 carbon atoms) unsaturated carboxylic acids such as acrylate, methacrylate, malate and fumarate, together with water-soluble monomers, in an amount of not more than 50% by weight relative to whole monomer, e.g., in an amount of 1 to 50% by weight.

According to the present invention, in the step (1), there is formed O/W emulsion, so-called "Oil in Water" by using the above-described polymerizable monomer and a water-soluble surfactant or water-soluble high-molecular dispersant, wherein the inner phase of the O/W emulsion is a hydrophilic phase and an outer phase thereof is a water phase containing the monomer.

As a water-soluble surfactant used in this step, any surfactant can be used as far as it is water-soluble. Examples of such surfactants concretely include anionic surfactants such as sulfates having 10 to 18 carbon atoms including sodium lauryl sulfate, sodium polyoxyethylenelauryl sulfate and the like; and nonionic surfactants havig a HLB value of not less than 7.0 such as fatty acid ester including polyoxyethyleneglycerin monostearate, polyoxyethyleneglycerin monoisostearate, rosin ester, polyoxyethylenerosin ester and the like. Examples of water-soluble high-molecular dispersants also include polyvinylalcohols whose saponification value is 60 to 95 mol.% and whose polymerization degree is 100 to 3000, modified polyvinylalcohols in which one or more sulfonic groups or carboxylic groups are incorporated in polyvinylalcohol, polyethyleneoxide, hydroxyethylcellulose, gum arabic and the like.

In the present invention, an O/W type emulsion is formed, e.g., by preparing an aqueous solution containing not less than 30%, preferably 35 to 50%, by weight of the above-described polymerizable monomer and 0.001 to 20%, preferably 0.01 to 10%, by weight of the water-soluble surfactant relative to the weight of the monomer, adding a hydrophobic organic compound to the aqueous solution and mixing them, although the O/W may be formed by any method. Examples of the hydrophobic organic compounds usable in this step include aliphatic hydrocarbons such as n-pentane, cyclopentane, n-hexane, cyclohexane, n-heptane and methylcyclohexane; aryl hydrocarbons such as benzene and toluene; aliphatic alcohols having 4 to 6 carbon atoms such as n-butylalcohol and n-amylalcohol; aliphatic ketones such as methyl ethyl ketone; and aliphatic esters such as ethyl acetate. These compounds can be used singly or in combination. Preferable amount of the hydrophobic organic compound is 1 to 150% by weight relative to the aqueous solution containing the monomer.

In the present invention, it is desirable to add a polymerization initiator to the O/W emulsion before the polymerization starts. Examples of the polymerization initiators include ketone peroxides such as methyl ethyl ketone peroxide and methyl isobutyl ketone peroxide; dialkyl peroxides such as di-tert-butyl peroxide and tert-butyl cumyl peroxide; alkyl peresters such as tert-butyl acetate and tert-butyl perisobutylate; peroxide such as hydrogen peroxide; persulfates such as potassium persulfate and ammonium persulfate; perchloric acid salts such as potassium perchlorate and sodium perchlorate; halogenic acid salts such as sodium and potassium; and azo-compounds such as 2-carbamoylazo-isobutyronitrile, 2,2'-azobis (N,N'-dimethyleneisobutylamidine) dihydrochloride, 2,2'-azobis (2-amidinopropane) dihydrochloride, 2,2'-azobis (N,N'-dimethyleneisobutylamindine), 4,4'-azobis (4-cyanopentanoic acid), azobis isobutyronitrile, 2,2'-azobis (4-methoxy-2,4-dimethylvaleronitrile), (1-phenylethyl) azodiphenylmethane, 2,2'-azobis isobutyronitrile, dimethyl-2,2' azobis isobutylate, 2,2'-azobis (2-methylbutyronitrile), 1,1'-azobis (1-cyclohexanecarbonitrile), 2,2'-azobis (2,4,4'-trimethylpentane), 2-phenylazo-2,4-dimethyl-4-methoxyvaleronitrile and 2,2'-azobis (2-methylpropane). These polymerization initiators can be used singly or in combination. The initiators are also used in an amount of 0.001 to 10 weight %, preferably 0.01 to 5 weight % relative to the amount of the monomer.

In the step (2) of the present invention, the O/W emulsion is added to a hydrophobic dispersing medium containing an oil-soluble surfactant or an oil-soluble high-molecular dispersant to form an O/W/O type emulsion. In other words, the O/W emulsion is dispersed in a hydrophobic phase (O). Such dispersing is conducted by a step for dispersing such as a mixing step carried out after the O/W emulsion is wholly added to the hydrophobic phase or a mixing step carried out while the O/W emulsion is gradually added to the hydrophobic phase.

Preferable oil-soluble surfactants used in this step are nonionic surfactants having an HLB of less than 7, for example, sorbitan fatty acid esters such as sorbitan oleate, sorbitan stearate and sorbitan laurate; sugar fatty acid esters such as sugar distearate; phtalates such as hexadecyl sodium phtalate and cetyl stearyl sodium phtalate.

Examples of the oil-soluble high-molecular dispersants also include cellulose ethers such as ethyl cellllulose, ethylhydroxyethyl cellulose and benzyl cellulose; cellulose esters such as cellulose acetate, cellulose butylate and cellulose acetate butyl; copolymers of oily ethylenically unsaturated monomers such as malein polybutadiene, malein polyethylene, malein polyalpha-olefin, a copolymer of acrylic acid-acryl stearate and a copolymer of styrene-diethylaminoethylmethacrylate.

It is preferable that these oil-soluble surfactants or oil-soluble high-molecular dispersant should have already been added to the hydrophobic dispersing medium in an amount of 0.1 to 25 weight %. As for the medium in this case, there can be used the same hydrophobic organic compounds as described in the formation of the O/W emulsion. In this connection, the medium may be the same hydrophobic compound as used in the most inner phase of the O/W/O emulsion. The amount of the hydrophobic dispersing medium is preferably 10 to 500 parts by weight relative to 100 parts by weight of O/W emulsion for reasons of economy and operability, although the amount is optional.

In the step (3) of the present invention, polymerization starts at the same time or after the O/W/O emulsion has been formed. The polymerization can be started by the conventional method, but it is preferable that the polymerization temperature be not less than 50° C. and the polymerization period be between 30 minutes and 6 hours.

The present invention basically employs the above-described steps. In addition, any of the conventional cross linking agents can be added either before, during or after the polymerization.

Such cross linking agents include, for example, polyallyl compounds such as N,N'-diallyl acrylamide, diallylamine, diallyl methacrylamide, diallyl phtalate, diallyl malate, diallyl terephthalate, triallyl cyanurate and triallyl phosphate; polyvinyl compounds such as divinylbenzene, N,N'-methylenebisacrylamide, ethyleneglycol diacrylate, ethyleneglycol dimethacrylate and glycerin trimethacrylate; polyglycidyl ethers such as ethyleneglycol glycidyl ether and polyethyleneglycol diglycidyl ether; haloepoxy compounds such as epichlorohydrin and -methylchlorohydrin; polyaldehydes such as glutaraldehyde and glyoxal; polyols such as glycerol, polyamines such as ethylenediamine; hydroxyvinyl compounds such as 2-hydroxylethyl methacrylate; and inorganic salts or organic metal salts which generate polyhydric ions such as calcium, magnesium, zinc and aluminum. Further, monoglycidyl compounds such as phenol polyoxyethylene glycidyl ether may be empolyed as modifiers. Any of the above-mentioned multifunctional cross linking agents or monofunctional cross linking agents such as monoglycidyl compound may be added in the present invention in an arbitrary amount depending on the properties which it is intended to impart to the final product of the water-absorbing resin. However, it is preferable for it to be added in an amount of 0.01 to 20%, preferably 0.01 to 10% relative to the dry weight of the resulting polymer. Furthermore, any compound such as a polymerization accelerator can be added to each phase of the O/W/O emulsion.

In the present invention, where the above-described cross-linking agent is added to the polymerization system, it is preferable to employ step (4) in which the cross-linking agent is added after the polymerization has completed in order to conduct cross-linking reaction on the surface of the polymer thus polymerized. In this case, it is preferable to adjust the water content of the porous polymer to not more than 40 weight %, preferably 1 to 30 weight % and thereafter to conduct a surface cross-linking by using a cross-linking agent enabling of reaction with the polymer. In this process, the term "surface cross-linking" means a cross-linking by which the cross-linking density of the surface of the polymer particles is made higher than that of interior of the polymer particles. Since the porous hydrophilic polymer is usually obtained having a water content of not less than 50 weight % in the step (3), the water content is adjusted to not more than 40 weight % by dehydration or drying. Where a compound vaporized with water is present in the polymerization mixture, examples of dehydration include conventional dehydration such as by azeotropy, a dehydration by azeotropy after an azeotropic compound is added to the mixture, and a dehydration by contacting the mixture with a hydrophilic organic solvent such as alcohols. As for drying methods, there are exemplified a method in which the polymerization mixture is directly dried; and method in which a solvent of the mixture is removed therefrom by decantation or centrifugal separation and then the resulting mixture is dried by a vaccum dryer or a fluid dryer. Therefore, the water content of the polymer is adjusted to not more than 40 weight % by the above methods, after which a cross-linking agent is added to the polymer to conduct the surface crosslinking.

Any cross-linking agent can be used in the surface cross-linking so long as the agent can react with a functional group of the polymer such as carboxyl group, carboxylate group or amino group. Such cross-linking agents include, for example, polyglycidyl ethers, haloepoxy compounds, polyaldehydes, polyols, polyamines and polyvalent metal salts as described above.

As for methods of conducting the surface polymerization, there can be employed any method so long as the cross-linking agent reacts with the polymer with the water content of the polymer being not more than 40% by weight. These methods include, for example, a method in which the resulting polymer is dehydrated by an azeotropic distillation or using a hydrophilic organic solvent and then a cross-linking agent is added to a polymer emulsion or a polymer suspension containing the polymer having a water content of not more than 40% by weight in the presence of a hydrophobic or a hydrophilic solvent, and if necessary, the polymer is subjected to heat treatment; a method in which a cross-linking agent is directly added to the dried polymer; a method in which a cross-linking agent is solubilized in a suitable amount of water or a mixed solvent of water and hydrophilic solvent and the resulting solution is added to the polymer; a method in which the dried polymer is dispersed in a hydrophobic or a hydrophilic solvent and then a cross-linking agent dissolved in a suitable amount of water is added to the resulting dispersion and, if necessary, the dispersion is further subjected to heat treatment; and a method in which a suitable amount of water is added to the polymer to bring the water content of the polymer up to a predetermined amount, and a cross-linking agent itself or a solution thereof is added to the polymer and, if necessary, the polymer is further subjected to heat treatment. It is preferable to conduct to heat treatment at a temperature of 30° to 150° C., and the solvent can be removed simultaneously therefrom as water.

Immediately after being polymerized or after the solvent has been removed by means of decantation or centrifugation following polymerization, a polymer manufactured by the above process is dried by a vacuum dryer or a fluidized dryer, and is ground or granulated, if necessary, before being supplied as a final product.

According to the process of the present invention, there can be manufactured a porous spherical polymer having a small apparent specific gravity and good elasticity as well as having good water-absorbing properties and permeability.

Furthermore, by employing a surface cross-linking step as step (4), the initial absorbing speed and gel strength of the polymer can be improved.

As a result, according to the present invention, there can be manufactured a spherical polymer having an average particle diameter of 20 to 500µ, preferably 40 to 300µ.

Therefore, the porous polymer of the present invention can be suitably applied to absorbing articles in such a way that the polymer is comprised in an absorbing layer of the article in many manners. Examples of such manner include the polymer being sandwiched between sheets of tissue paper in which the polymer is preferably used in a basis weight of 10 to 200 g/m$^2$; the polymer being mixed with cottonlike pulp in which preferable weight ratio of the cottonlike pulp to the polymer is 20/1 to 1/2; and the polymer being adhered on the surface of a thermoplastic sheet. The absorbing layer thus prepared can be located in any position of the interior of the conventional absorbing articles; for example, it can be located near the surface of the article or near the bottom thereof.

More concretely, examples of the absorbing articles include many articles in which each absorbing layer of the following (I) to (V) is located on a waterproofing sheet (polyolefin sheet, or tissue paper the inside of which is coated with polyolefin) and thereafter the whole is covered with a body-fluid-permeable sheet.

(I) a pressed cottonlike pulp being positioned on a polymer sheet in which the absorbing polymer is sandwiched between two sheets of tissue paper;

(II) one piece to 20 pieces of tissue paper being positioned on the polymer sheet;

(III) the polymer being added in a cottonlike pulp;

(IV) the polymer sheet being positioned on the above (III); and (V) Staple fibers being positioned on each of (I) to (IV) to provide good cushioning characteristics.

In this case, any kind of sheet can be used as the body-fluid-permeable sheet, but it is preferable to use a nonwoven fabric, more preferbly a hydrophobic nobinder nonwoven fabric having a base weight of 4 to 40 g/m$^2$.

In this specification, the absorbing articles include sanitary napkins, paper diapers, bedsheets for the sick, and tampons. When the absorbing aricles are used as sanitary napkins or paper diapers, it is preferable to provide adhesive tape thereon in the same manner as coventional ones.

Furthermore, since the gel structure of the polymer manufactured by the present invention does not deteriorate even when used for a long time, the polymer can be suitably used in various industrial applications as a water retaining agent in agriculture and gardening and as a water blocking agent in civil engineering and construction, and the polymer can be applied to cosmetics in which the form, elasticity, water-absorbing properies and permeability of the polymer are important. Furthermore, the polymer can be used in other applications such as in dew condensation and ion exchange resins in which moisture-absorbing properties and permeability of the polymer are important.

In addition, the polymer prepared by the present invention can be used in various application after being treated with an additive such as a colorant or perfume, or after having a filler added thereto, and also after being combined with a different material such as paper or fiber. Furthermore, depending on the characteristics of the polymerizable monomer to be used, there can be manufactured various porous polymers having other characteristics besides a water absorbing polymer.

The present invention will be further explained with reference to the following non-limitative Examples.

EXAMPLE 1

300 g of cyclohexane and 3 g of ethyl cellulose (manufactured by Hercules under the brand name N-50) were placed in a 1 liter flask and stirred, said flask being provided with an agitator, a reflux condenser, a dropping funnel, and a pipe for introducing nitrogen gas at its inlet. Nitrogen gas was then blown into the flask so as to release dissolved oxygen, and the flask was warmed to a temperature of 70° C.

43 g of sodium hydroxide was dissolved in 130 g of water in another flask. 100 g of acrylic acid (AA) was added to this flask. 0.16 g of ammonium persulfate (APS), 4 g of modified polyvinylalcohol (manufactured by The Nippon Synthetic Chemical Industry Co. Ltd. under the brand name OKS-3266), 25 mg of ethyleneglycol diglycidyl ether and 54 g of hexane were then dissolved in this solution. Nitrogen gas was blown into this flask so that the dissolved oxygen was released, thus preparing an aqueous solution of monomer (O/W emulsion).

Subsequently, the O/W emulsion was dripped into the first flask for 1 hour while the flask was agitated at a rate of 400 rpm, and polymerization was carried out for 3 hours. The resulting polymer was dried at a temperature of 80° C. under reduced pressure so as to obtain a porous spherical polymer (void volume: 0.12 ml/g; average particle diameter: 200μ)

EXAMPLE 2

A porous spherical polymer (void volume: 0.05 ml/g; average particle diameter: 180μ) was obtained by the same method as set forth in Example 1, except that 50 mg of sodium dodecylbenzenesulfonate was used instead of modified polyvinylalcohol and 27 g of ethyl acetate was also used instead of hexane.

EXAMPLE 3

A porous spherical polymer (void volume: 0.20 ml/g; average particle diameter: 220μ) was obtained by the same method as set forth in Example 1, except that 4 g of a partially saponified polyvinyl alcohol (manufactured by The Nippon Synthetic Chemical Industry Co. Ltd. under the trade name GH-17) was used instead of modified polyvinylalcohol and 81 g of cyclohexane was also used instead of hexane.

EXAMPLE 4

A porous spherical polymer (void volume: 0.11 ml/g; average particle diameter: 200μ) was obtained by the same method as set forth in Example 1, except that 80 g of acrylic acid and 20 g sodium acrylamidomethylpropanesulfate (AMPS) was used instead of acrylic acid and the amount of sodium hydrate was changed to 34 g from 43 g, and 4 g of rosin (EO)$_{15}$ ester was used instead of modified polyvinylalcohol. In this case, (EO)$_{15}$ means addition of an average of 15 moles of ethyleneoxide.

EXAMPLE 5

A porous spherical polymer (void volme: 0.10 ml/g; average particle diameter: 210μ) was obtained by the same method as set forth in Example 1, except that 80 g of acrylic acid and 20 g of dimethylaminoethylmethacrylate were used instead of 100 g acrylic acid, and the amount of sodium hydrate was changed to 34 g from 43 g, and 54 g of cyclohexane and 0.2 g of glycerine (EO)$_{30}$ isostearate were used instead of hexane and modified polyvinylalcohol, respectively.

COMPARATIVE EXAMPLE 1

300 g of cyclohexane and 3 g of ethyl cellulose (manufactured by Hercules under the brand name N-50) were placed in a 1 l flask and stirred said flask being provided with an agitator, a reflux condenser, a dropping funnel, and a pipe for introducing nigrogen gas at its inlet. Nitrogen gas was then blown into the flask so as to release dissolved oxygen, and the flask was warmed to a temperature of 70° C.

43 g of sodium hydroxide was dissolved in 130 g of water in another flask. 100 g of acrylic acid (AA) was added to this flask. 0.16 g of ammonium persulfate (APS) and 25 mg of ethyleneglycol diglycidyl ether was then dissolved in this solution. Nitrogen gas was blown into this flask so that the dissolved oxygen was released, thus preparing an aqueous solution of monomer.

Subsequently, the monomer solution was dripped into the first flask for 1 hour while the flask was agitated at a rate of 400 rpm, and polymerization was carried out for 3 hours. Thereafter, the resulting polymer was dried at a temperature of 80° C. under reduced pressure so as to obtain a porous spherical polymer (void volume: 0 ml/g; average particle diameter: 210μ).

COMPARATIVE EXAMPLE 2

A spherical polymer (void volume: 0 ml/g; average particle diameter: 200μ) was obtained by the same method as set forth in Comparative Example 1, except that a modified polyvinylalcohol was not used.

Properties of the polymers obtained by Examples 1 to 5 and Comparative Examples 1 and 2 are shown in Table 1. In this Table, the initial water absorbing speed was determined by the following:

INITIAL WATER ABSORBING SPEED 0.3 g of polymer was charged in a tea-bag type paper bag measuring 6 by 8 cm and the bag was stood vertically to transfer the polymer to the bottom of the bag. The bag was vertically immersed for one minute in physiologic saline charged in a 300 ml beaker. After immersion for one minute, it was removed, drained, and weighed. The weight of another bag which contained no polymer, and which was used as a control was measured using the same method. The thus obtained weight of the sample from which the weight of the control had been subtracted was divided by the weight of the polymer so as to obtain the weight per gram of the polymer, which is used as the initial water absorbing speed.

as to release dissolved oxygen, and the flask was warmed to a temperature of 70° C.

43 g of sodium hydroxide was dissolved in 130 g of water in another flask. 100 g of acrylic acid (AA) was added to this flask. 0.16 g of ammonium persulfate (APS), 1.2 g partially saponified polyvinylalcohol (manufactured by The Nippon Synthetic Chemical Industry Co. Ltd. under the brand name GH-17), 122 mg of ethyleneglycol diglycidyl ether (EGDG) and 80 g of cyclohexane were then dissolved in this solution. Nitrogen gas was blown into this flask so that the dissolved oxygen was released, thus preparing an aqueous solution of monomer (O/W emulsion).

Subsequently, the O/W emulsion was dripped into the first flask for 1 hour while the flask was agitated at a rate of 400 rpm, and polymerization was carried out for 3 hours. Thereafter, using a dehydration tube, the temperature of the surrounding water bath was raised to 85° C. so as to cause dehydrate by azeotropic distillation and water was removed from the polymer until the water content of the polymer reached 15.0% by weight. 122 mg of ethyleneglycol diglycidyl ether dissolved in 2 g of water was added to this flask containing the polymer dispersion. After reacting it with the polymer for 2 hours at a temperature of 70° C., cyclohexane was distilled off. The resulting polymer was dried at a temperature of 80° C. under a reduced pressure so as to obtain a porous spherical polymer (void volume: 0.20 ml/g; average particle diameter: 200μ).

TABLE 1

| | O/W | | | | | Properties of polymer | |
|---|---|---|---|---|---|---|---|
| | Vinyl monomer | Water-soluble surfactant or high-molecular dispersant | | Hydrophobic organic compound | | Apparent specific gravity ($g/cm^3$) | Initial water-absorbing speed (g/g polymer) |
| | | Kind | (%) | Kind | (%) | | |
| Example 1 | AA | Sulfonated polyvinylalcohol | 4 | Hexane | 20 | 0.68 | 14 |
| Example 2 | AA | Sodium dodecylsulfonate | 0.05 | Ethyl acetate | 10 | 0.78 | 10 |
| Example 3 | AA | Polyvinylalcohol | 4 | Cyclohexane | 30 | 0.60 | 16 |
| Example 4 | AA/AMPS | Rosin $(EO)_{15}$ ester | 4 | Hexane | 20 | 0.69 | 12 |
| Example 5 | AA/DM | Isostearic $(EO)_{30}$ glycerin ester | 0.2 | Cyclohexane | 20 | 0.70 | 12 |
| Comparative Example 1 | AA | — | — | — | — | 0.91 | 3 |
| Comparative Example 2 | AA | Solfonated polyvinylalcohol | 4 | — | — | 0.90 | 5 |

Figure 1:
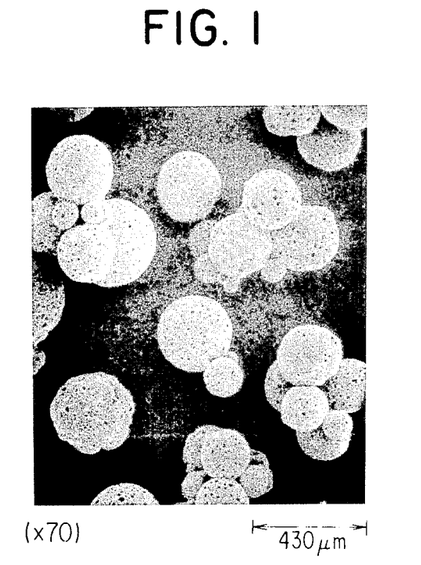
FIGS. 1 and 2 are photomicrographs (FIG. 1: ×70, FIG. 2: ×300) of porous polymer particles of the present invention prepared by Example 1.
Figure 2:
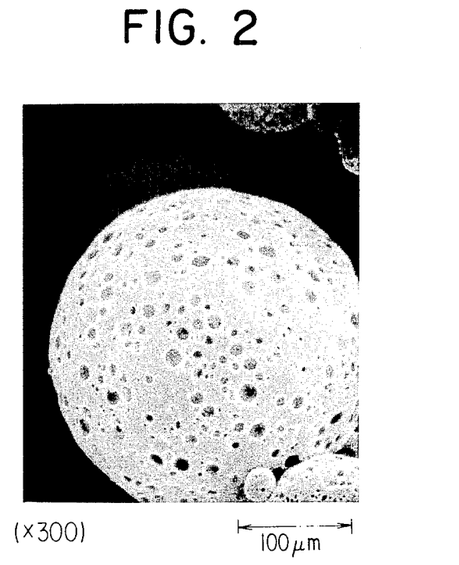
Figure 3:
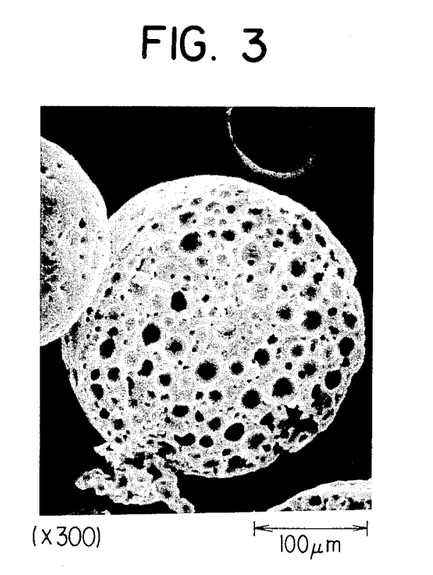
FIG. 3 is a photomicrograph (×300) of a cross section of the same.
Figure 4:
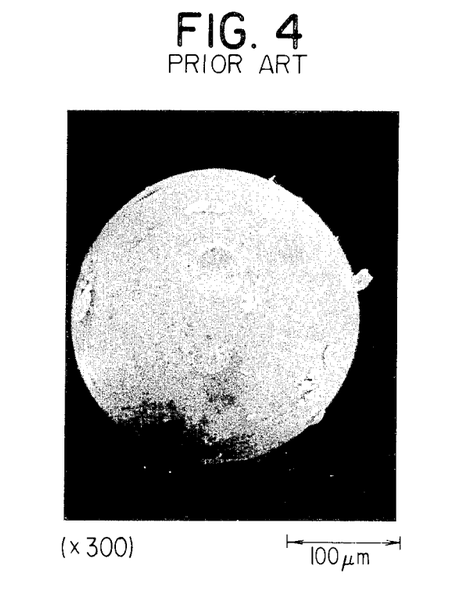
FIG. 4 is a photomicrograph (×300) of the conventional polymer particles prepared by Comparative Example 1.
Figure 5:
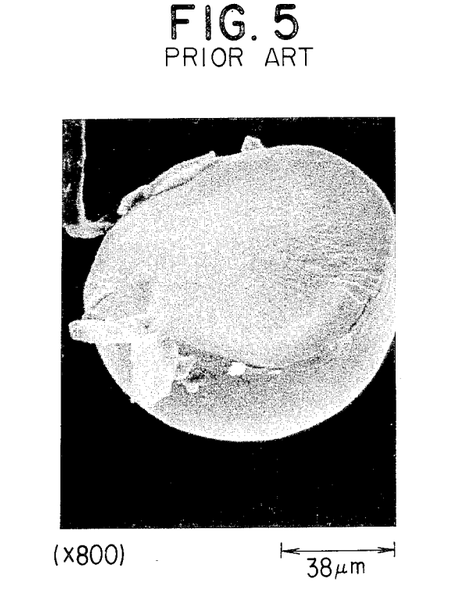
FIG. 5 is a photomicrograph (×800) of a cross section of the particles prepared by Comparative Example 1.

Photomicrographs (×70 and ×300) of the porous polymer particles prepared by Example 1 according to the present invention are shown in FIGS. 1 and 2 respectively. A photomicrograph (×300) of a cross section of the same is shown in FIG. 3. On the other hand, a photomicrograph (×300) of the polymer particles prepared by Comparative Example 1 is shown in FIG. 4 and a photomicrograph (×800) of a cross section of the same as shown in FIG. 5.

As in clear from Table 1 and FIGS. 1 to 5, there can be obtained polymers having good properties by polymerizing after forming O/W/O emulsion according to the present invention.

EXAMPLE 6

300 g of cyclohexane and 3 g of ethyl cellulose (manufactured by Hercules under the brand name N-50) were placed in a 1 l flask and stirred, said flask being provided with an agitator, a reflux condenser, a dropping funnel, and a pipe for introducing nitrogen gas at its inlets. Nitrogen gas was then blown into the flask so

EXAMPLE 7

A porous spherical polymer (void volume: 0.08 ml/g; average particle diameter; 200μ) was obtained by the same method as set forth in Example 6, except that 100 mg of $(EO)_{10}$ sorbitan monooleate (manufactured by Nikko Chemical Co. under the trade name of TO-10) and 54 g of hexane were used instead of partially saponified polyvinylalcohol and 82 g of cyclohexane, respectively, and 5% aluminium sulfate was also used instead of ethyleneglycol diglycidyl ether when the water content of the polymer was 10% by weight after dehydration by azeotropic distillation.

EXAMPLE 8

A porous spherical polymer (void volume: 0.20 ml/g; average particle diameter: 200μ) was obtained by the same method as set forth in Example 6, except that surface cross-linking was conducted on a polymer having a water content of 58% by weight without dehydration (without using the dehydration tube).

EXAMPLE 9

A porous spherical polymer (void volume: 0.08 ml/g; average particle diameter: 200μ) was obtained by the same method as set forth in Example 7, except that surface cross-linking was conducted on a polymer having a water content of 58% by weight without dehydration (without using the dehydration tube).

The properties of the polymer prepared in Examples 6 to 9 are shown in Table 2. In this Table, gel strength of the polymer was determined by the following:

GEL STRENGTH 2 g of a polymer was placed in a 100 ml beaker, and was then moistened with 2 g of methanol. 40 g of ion-exchange water was poured over the resin in one movement. The beaker was sufficiently shaken so that no lumps of polymer were felt and the water was absorbed evenly, to prepare a sample. Subsequently, the thus-prepared sample ws raised at a speed of 2 cm/min using a rheometer (NRM-2002J, manufactured by Fudo Kogyo K.K.), and the stress, which is to be used as the gel strength, was measured 10 seconds after the gel surface made contact with an adaptor (on a 10-mm diameter disc). The larger this value, the stronger the water-absorbing gel).

TABLE 2

| | | Properties of polymer | | |
|---|---|---|---|---|
| No. | Water content of a polymer to be surface-crosslinked | Apparent specific gravity (g/cm$^3$) | Initial water-absorbing speed (g/g polymer) | Gel strength (g/cm$^2$) |
| 6 | 15 | 0.65 | 36 | 81 |
| 7 | 10 | 0.74 | 27 | 75 |
| 8 | 58 | 0.65 | 16 | 59 |
| 9 | 58 | 0.74 | 15 | 56 |

As is clear from Table 2, the initial water absorbing speed and a gel strength of the polymer are remarkably increased by conducting a surface cross-linking on a porous polymer having a water content of not more than 40% by weight.

EXAMPLE 10

300 g cyclohexane and 3 g of ethyl cellulose (manufactured by Hercules under the brand name N-50) were placed in a 1 liter four-necked flask and stirred, said flask being provided with an agitator, a reflux condenser, a dropping funnel, and a pipe for introducing nitrogen gas at its inlets. Nitrogen gas was then blown into the flask so as to release dissolved oxygen, and the flask was warmed to a temperature of 70° C.

43 g of sodium hydroxide was dissolved in 159 g of water in another flask. 100 g of acrylic acid (AA) was added to this flask. 0.16 g of ammonium persulfate (APS), 3.0 g of carboxylated polyvinylalcohol (manufactured by The Nippon Synthetic Chemical Industry Co. Ltd. under the brand name T-350), and 80 g of cyclohexane were then dissolved in this solution. Nitrogen was blown into this flask so that the dissolved oxygen was released, thus preparing an aqueous solution of monomer (O/W emulsion).

Subsequently, the O/W emulsion was dripped into the first flask for 2 hours while the flask was agitated at a rate of 400 rpm, and polymerization was carried out for 3 hours. Thereafter, 0.3 g of ethyleneglycol diglycidyl ether (produced by NAGASE CHEMICAL INDUSTRY Co. under the brand name DENACOL EX-810) dissolved in 2.7 g of water was added to this flask containing the polymer dispersion. After reacting it with the polymer for 2 hours at a temperature of 70° C., cyclohexane was distilled off. The resulting polymer was dried at a temperature of 80° C. under a reduced pressure to obtain a porous spherical polymer (void volume: 0.21 ml/g; average particle diameter: 150μ).

EXAMPLE 11

A porous spherical polymer (void volume: 0.40 ml/g; average particle diameter: 150μ) was obtained by the same method as set forth in Example 10, except that 0.5 g of partially saponified polyvinylalcohol (manufactured by The Nippon Synthetic Chemical Industry Co. Ltd. under the brand name GH-17), 150 g of hexane and 0.4 g of diglycerin polyglycidyl ether (produced by NAGASE CHEMICAL INDUSTRY Co. under the brand name DENACOL EX-512) were dissolved in 4.1 g of water and used, instead of 3.0 g of carboxylated polyvinylalcohol, 80 g of cyclohexane, and 0.3 g of ethyleneglycol diglycidylether, respectively.

EXAMPLE 12

300 g of cyclohexane and 4 g of ethyl cellulose (manufactured by Hercules under the brand name N-22) were placed in a 1 liter four-necked flask and stirred, said flask being provided with an agitator, a reflux condenser, a dropping funnel, and a pipe for introducing nitrogen gas at its inlet. Nitrogen gas was then blown into the flask so as to release dissolved oxygen, and the flask was warmed to a temperature of 70° C. 43 g of sodium hydroxide was dissolved in 130 g of water in another flask. 100 g of acrylic acid (AA) was added to this flask to prepare a solution having 45% of a monomer concentration and 75% of neutralization degree.

To this solution, 10 g of caboxylated polyvinylalcohol (produced by The Nippon Synthetic Chemical Industry Co. Ltd. under the brand name T-350) dissolved in 40 g of water was added to increase the viscosity thereof, and then 0.1 g of 2,2'-azobis (2-amidinopropane) dihydrochloride as an initiator was added. A large amount of nitrogen gas was blown into the solution to obtain an aqueous monomer solution containing foam.

Subsequently, the monomer solution was dripped over 2 hours into the dispersant in the flask with agitation at a rate of 400 rpm. Polymerization reaction was carried out at 70° C. for additional 2 hours. 0.3 g of ethyleneglycol diglycidylether (produced by NAGASE CHEMICAL INDUSTRY Co. under the brand name DENACOL EX-810) dissolved in 2.7 g of water was added and reacted at 70° C. for 2 hours with agitation. After cooling, cyclohexane was removed by decantation. The residue was mixed with 500 g of methanol with agitation and dehydrated for one hour, and then filtered. The product was dried by a hot air dryer at 120° C. for 2 hours to give a porous spherical polymer (void volume: 0.12 ml/g; average particle diameter: 200μ).

COMPARATIVE EXAMPLE 3

The procedures of Example 10 were repeated to obtain a polymer having no void and having an average particle diameter of 200μ; except that 80 g of cyclohexane was not used when an aqueous monomer solution (O/W emulsion) was prepared.

COMPARATIVE EXAMPLE 4

The procedures of Example 10 were repeated to obtain a polymer having no void and having an average particle diameter of 150μ, except that 3.0 g of carboxylated polyvinylalcohol and 80 g of cyclohexane were not used when an aqueous monomer solution (O/W emulsion) was prepared.

EXAMPLE 13

0.5 g of each polymer prepared in Examples 6, 7, 10, 11 and 12 and Comparative Examples 3 and 4 was uniformly scattered between 2 pieces of tissue paper (7 cm by 16 cm) and pressing and contact bonding were then performed using an embossing roll so as to prepare a polymer sheet. The resulting polymer sheet was sandwiched between two sets of 10 pieces of tissue papers having the same size as that of the polymer sheet, and the whole was then covered with a piece of non-woven fabric sheet to form a sanitary napkin (an absorbing article). The napkin was put on a sieve of 8 mesh, and an acryl plate and a weight of 5 kg (45 g/cm$^2$(were then placed on the napkin. It was immersed for 5 minutes in 2 l of artificial menstrual blood charged in a stainless steel basin. It was then remained, and drained on a metal mesh for 3 minutes before being weighed. A napkin similar to the above, except that it did not contain the polymer, was formed as described above, subjected to determination of its blood absorbing properties by the same method as described above.

The thus obtained weight of each of the samples from which the weight of the control had been subtracted was divided by the weight of the polymer to obtain the weight per gram of the polymer.

EXAMPLE 14

0.7 g of each polymer prepared in Examples 6, 7, 10, 11 and 12 and Comparative Examples 3 and 4 was uniformly scattered between 2 pieces of crashed pulp (7 by 16 cm, 200 g/m$^2$) and this was the wholly covered with a piece of non-woven fabric sheet to form a paper diaper (an absorbing article). The diaper was put on a sieve of 8 mesh, and an acryl plate and a weight of 5 kg (45 g/cm$^2$) was placed on the diaper. These Immersion for 5 minutes in 5 l of artificial urine charged in a stainless steel basin followed. It was then removed and drained on a metal mesh for 3 minutes before being weighed. A diaper similar to the above, except that it did not contain the polymer, was formed as described above, and subjected to determination of its urine absorbing properties by the same method as described above so as to obtain a control value.

The thus obtained weight of the sample from which the weight of the control had been subtracted was divided by the weight of the polymer to obtain the weight per gram of the polymer.

The properties of absorbing articles formed by Examples 10 and 11 are shown in Table 3.

TABLE 3

|  | Example in which a polymer was prepared | Void volume (ml/g) | Absorbing amount under a pressure of 45 g/cm$^2$ (g/g - P 5 minutes) | |
|---|---|---|---|---|
|  |  |  | Napkin | Paper diaper |
| Invention | Example 6 | 0.65 | 26 | 30 |
|  | Example 7 | 0.74 | 23 | 27 |
|  | Example 10 | 0.21 | 23 | 26 |
|  | Example 11 | 0.40 | 25 | 28 |
|  | Example 12 | 0.12 | 21 | 24 |
| Comparison | Comparative Example 3 | 0 | 16 | 19 |
|  | Comparative Example 4 | 0 | 15 | 18 |

As is clear from Table 3, absorbing articles of the present invention can absorb a large amount of body fluid under a pressed condition.

What is claimed is:

1. A process for manufacturing a porous polymer particles comprising the steps of:
   (1) forming O/W emulsion by using a water-soluble surfactant or a water-soluble high-molecular dispersant wherein an inner phase of the O/W emulsion is a hydrophobic phase and a outer phase thereof is a water phase containing at least one water-soluble polymerizable monomer;
   (2) adding said O/W emulsion to a hydrophobic dispersing medium containing an oil-soluble surfactant or an oil-soluble high-molecular dispersant to form O/W/O emulsion; and
   (3) polymerizing the monomer.

2. A process as set forth in claim 1, wherein the water-soluble polymerizable monomer is selected from olefin unsaturated carboxylic acids, olefin unsaturated sulfonic acids, olefin unsaturated amines and olefin unsaturated ethers.

3. A process as set forth in claim 1, wherein the water-soluble surfactant is selected from sulfates having 10 to 18 carbon atoms and nonionic surfactants having an HLB value of not less than 7.0.

4. A process as set forth in claim 1, wherein the water-soluble high-molecular dispersant is selected from polyvinylalcohols whose saponification value is 60 to 90 mol.% and whose polymerization degree is 100 to 3000, modified polyvinylalcohols in which one or more sulfonic groups or carboxylic groups are incorporated in polyvinylalcohol, polyethyleneoxide, hydroxyethylcellulose and gum arabic.

5. A process as set forth in claim 1, wherein the O/W emulsion is formed by preparing an aqueous solution containing not less than 30% by weight of the polymerizable monomer and 0.001 to 20% by weight of the water-soluble surfactant relative to the weight of the monomer, adding a hydrophobic organic compound to the aqueous solution and mixing them.

6. A process as set forth in claim 5, the hydrophobic organic compound is selected from aliphatic hydrocarbons, aryl hydrocarbons, aliphatic alcohols having 4 to 6 carbon atoms, aliphatic ketones and aliphatic esters.

7. A process as set forth in claim 1, wherein a polymerization initiator is added to the O/W emulsion before the polymerization starts.

8. A process as set forth in claim 1, wherein the oil-soluble surfactant is a nonionic surfactant having an HLB value of less than 7.

9. A process as set forth in claim 1, wherein the oil-soluble high-molecular dispersant is selected from cellulose ethers, cellulose esters and copolymers of oily ethylenically unsaturated monomers.

10. A process as set forth in claim 1, wherein the oil-soluble surfactant or the oil-soluble high-molecular dispersant is added to the hydrophobic dispersing medium in an amount of 0.1 to 25 weight %.

11. A process as set forth in claim 1, wherein the amount of the hydrophobic dispersing medium is 10 to 500 parts by weight relative to 100 parts by weight of the O/W emulsion.

12. A process as set forth in claim 1, wherein a water content of the resulting polymer is further adjusted to 40% by weight and then a cross-linking reaction is conducted on the surface of the polymer by adding a cross-linking agent.

13. A process as set forth in claim 12, wherein the amount of the cross-linking agent is 0.01 to 20% by weight relative to dry weight of the polymer.

14. A process as set forth in claim 1, wherein a solvent is distilled off after the polymerization is completed, and the polymer is dried.

* * * * *